United States Patent
Hoshino et al.

(10) Patent No.: US 7,544,494 B2
(45) Date of Patent: *Jun. 9, 2009

(54) VITAMIN C FROM SORBOSONE

(75) Inventors: Tatsuo Hoshino, Kamakura (JP); Taro Miyazaki, Fujisawa (JP); Teruhide Sugisawa, Riehen (CH)

(73) Assignee: DSM IP Assets B.V., TE Heerlen (NL)

( * ) Notice: Subject to any disclaimer, the term of this patent is extended or adjusted under 35 U.S.C. 154(b) by 52 days.

This patent is subject to a terminal disclaimer.

(21) Appl. No.: 10/528,885

(22) PCT Filed: Sep. 22, 2003

(86) PCT No.: PCT/EP03/10495

§ 371 (c)(1),
(2), (4) Date: Aug. 26, 2005

(87) PCT Pub. No.: WO2004/029269

PCT Pub. Date: Apr. 8, 2004

(65) Prior Publication Data

US 2006/0121582 A1    Jun. 8, 2006

(30) Foreign Application Priority Data

Sep. 27, 2002    (EP)    ................................. 02021624

(51) Int. Cl.
*C12N 9/02* (2006.01)
*C12N 9/04* (2006.01)
*C12N 9/06* (2006.01)

(52) U.S. Cl. .................. 435/126; 435/189; 435/190; 435/191

(58) Field of Classification Search .................. 435/126
See application file for complete search history.

(56) References Cited

U.S. PATENT DOCUMENTS

| 6,242,233 B1 * | 6/2001 | Hoshino et al. | ............. 435/190 |
| 7,341,854 B2 * | 3/2008 | Hoshino et al. | ............. 435/126 |
| 2005/0153412 A1 * | 7/2005 | Hoshino et al. | ............. 435/189 |

FOREIGN PATENT DOCUMENTS

| EP | 0 518 136 | 12/1992 |
| EP | 0 832 974 | 4/1998 |
| EP | 0 922 759 | 6/1999 |
| EP | 1 026 257 | 8/2000 |
| GB | 466548 | 5/1937 |
| WO | WO 03/089634 | 10/2003 |
| WO | WO 03/104445 | 12/2003 |

OTHER PUBLICATIONS

Loewus, M.W. et al., "Conversion of $_L$-Sorbonone to $_L$-Ascorbic Acid by a NADP-Dependent Dehydrogenase in Bean and Spinach Leaf[1]," *Plant Physiol*, vol. 94, pp. 1492-1495 (1990).

* cited by examiner

*Primary Examiner*—Herbert J. Lilling
(74) *Attorney, Agent, or Firm*—Bryan Cave LLP

(57) ABSTRACT

The present invention relates to a process for the production of vitamin C from L sorbosone using an aldehyde dehydrogenase which is isolated from *Gluconobacter oxydans* DSM 4025 (FERM BP-3812), said enzyme having the following physicochemical properties: (a) molecular weight of 150,000±6,000 Da or 230,000±9,000 Da (consisting of 2 or 3 homologous subunits, each subunit having a molecular weight of 75,000±3,000 Da); (b) substrate specificity as active on aldehyde compounds; (c) Cofactors are pyrroloquinoline quinone and heme c; (d) Optimum pH between 6.4 and 8.2 for vitamin C production from L-sorbosone; and (e) as inhibitors $Co^{2+}$, $Cu^{2+}$, $Fe^{2+}$, $Ni^{2+}$, $Zn^{2+}$, monoiodoacetate and ethylendiamine tetraacetic acid. The process is performed in the presence of a suitable electron acceptor and the vitamin C isolated from the reaction mixture.

8 Claims, No Drawings

VITAMIN C FROM SORBOSONE

This application is the National Stage of International Application No. PCT/EP2003/010495, filed Sep. 22, 2003.

The present invention relates to a process for producing L-ascorbic acid (vitamin C) from L-sorbosone utilizing an aldehyde dehydrogenase, i.e., L-sorbosone dehydrogenase, purified from the cell free extract of *Gluconobacter oxydans* DSM 4025 (FERM BP-3812).

The above mentioned enzyme was disclosed in EP 0 922 759 A2 and catalyzes the oxidation reaction of L-sorbosone to 2-keto-L-gulonic acid (2-KGA).

Vitamin C is a very important and indispensable nutrient factor for human beings. It is industrially synthesized by the "Reichstein method". D-glucosone and L-sorbosone are putative intermediates of vitamin C biosynthesis in bean and spinach, and the nicotinamide adenine dinucleotide phosphate (NADP)-dependent enzyme catalyzing the oxidation reaction of L-sorbosone to vitamin C has been partially purified. However, there have been no reports on the conversion of L-sorbosone to vitamin C by using the enzyme originating from a bacterial source. Surprisingly, it was found that this enzyme can convert L-sorbosone not only to 2-KGA, but also to vitamin C under specific reaction.

The present invention provides a process for producing vitamin C from L-sorbosone comprising contacting L-sorbosone with a purified L-sorbosone dehydrogenase having the following physico-chemical properties:
(a) Molecular weight: 150,000±6,000 Da or 230,000±9,000 Da (consisting of 2 or 3 homologous subunits, each subunit having a molecular weight of 75,000±3,000 Da);
(b) Substrate specificity: active on aldehyde compounds;
(c) Cofactors: pyrroloquinoline quinone and heme c;
(d) Optimum pH: 6.4 to 8.2 for the production of vitamin C from L-sorbosone;
(e) Inhibitors: $Co^{2+}$, $Cu^{2+}$, $Fe^{2+}$, $Ni^{2+}$, $Zn^{2+}$, monoiodoacetate and ethylenediamine tetraacetic acid;

in the presence of an electron acceptor, and isolating the resulting vitamin C from the reaction mixture.

For the purpose of the present invention, the term "purified" also includes isolated from its natural environment.

Oxidation of L-sorbosone to vitamin C in the presence of an electron acceptor occurs according to the following reaction equation:

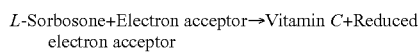

The enzyme does not work with oxygen as an electron acceptor. In addition nicotineamide adenine dinucleotide (NAD) and nicotineamide adenine dinucleotide phosphate (NADP) are not suitable electron acceptors. However, other conventional electron acceptors can be utilized in conjunction with the process of this invention. (2,6-dichlorophenolindophenol (DCIP), phenazine methosulfate (PMS), ferriccyanide and cytochrome c are preferred electron acceptors.

The enzyme assay may be performed as follows:

a) Product (Vitamin C) Assay of L-sorbosone Dehydrogenase Activity

A reaction mixture consisting of 1.0 mM PMS, 25 mM potassium phosphate buffer (pH 7.0), 1.0 µM pyrroloquinoline quinone (PQQ), 1.0 mM $CaCl_2$, 50 mM L-sorbosone and enzyme solution in a final volume of 100 µl with water is prepared just before the assay. The reaction is carried out at 30° C. for 60 min unless otherwise stated. The amount of vitamin C produced is measured at a wavelength of 264 nm by a high performance liquid chromatography (HPLC) which is coupled with a UV detector (TOSOH UV8000; TOSOH Co., Kyobashi 3-2-4, Chuo-ku, Tokyo, Japan), a dualpump (TOSOH CCPE; TOSOH Co.), an integrator (Shimadzu C-R6A; Shimadzu Co., Kuwahara-cho 1, Nishinokyo, Chukyo-ku, Kyoto, Japan) and a column (YMC-Pack Polyamine-II, YMC, Inc., 3233 Burnt Mill Drive Wilimington, N.C. 28403, U.S.A.). The amount of 2-KGA produced is measured by HPLC. One unit of the enzyme activity is defined as the amount of the enzyme that produces 1 mg vitamin C or 2-KGA in 60 min in the reaction mixture.

b) Photometrical Assay of L-sorbosone Dehydrogenase Activity

A reaction mixture consisting of 0.1 mM DCIP, 1.0 mM PMS, 50 mM potassium phosphate buffer (pH 7.0), 1.0 µM PQQ, 2.0 mM L-sorbosone and enzyme solution in a final volume of 100 µl with water is prepared just before the assay. The reaction is started at 25° C. with L-sorbosone, and the enzyme activity is measured as the initial reduction rate of DCIP at 600 nm. One unit of the enzyme activity is defined as the amount of the enzyme catalyzing the reduction of 1 µmole DCIP per minute. The extinction coefficient of DCIP at pH 7.0 is taken as 14.2 $mM^{-1}$, A reference cuvette contains all the above constituents except of L-sorbosone.

The L-sorbosone dehydrogenase of the present invention can be isolated from a cell free extract of *G. oxydans* DSM 4025 (PERM BP-3812) in accordance with the methods described in EP 0 922 759 A2.

Thus, the present invention provides a process for producing vitamin C from L-sorbosone as described above, wherein the L-sorbosone dehydrogenase is derived from the strain *Gluconobacter oxydans* DSM 4025 (FERM BP-3812), a microorganism belonging to the genus *Gluconobacter* having the identifying characteristics of *G. oxydans* DSM 4025 (FERM BP-3812) or mutants thereof.

*G. oxydans* DSM 4025 was deposited at the Deutsche Sammlung von Mikroorganismen und Zellkulturen (DSMZ) in Göttingen (Germany), based on the stipulations of the Budapest Treaty, under DSM No. 4025 on Mar. 17, 1987. The depositor was The Oriental Scientific Instruments Import and Export Corporation for Institute of Microbiology, Academia Sinica, 52 San-Li-He Rd., Beijing, Peoples Republic of China. The effective depositor was said Institute, of which the full address is The Institute of Microbiology, Academy of Sciences of China, Haidian, Zhongguancun, Beijing 100080, People's Republic of China.

A subculture of the strain has also been deposited at the National Institute of Advanced Industrial Science and Technology (AIST), Tsukuba Central 6, 1-1-1 Higashi, Tsukuba, Ibaraki 305-8566, Japan, also based on the stipulations of the Budapest Treaty, under the deposit No. FERM BP-3812 on Mar. 30, 1992. The depositor is Nippon Roche K.K., 6-1, Shiba 2-chome, Minato-ku, Tokyo 105-8532 Japan. This subculture is also most preferably used in the present invention.

The enzyme may be isolated and purified after the cultivation of the microorganism, *G. oxydans* DSM 4025 (FERM BP-3812) as follows:

(1) Cells are harvested from the liquid culture broth by centrifugation or filtration.
(2) The harvested cells are washed with water, physiological saline or a buffer solution having an appropriate pH.
(3) The washed cells are suspended in the buffer solution and disrupted by means of a homogenizer, sonicator or French press or by treatment with lysozyme and the like to give a solution of disrupted cells.

(4) The said enzyme is isolated and purified from the cell-free extract of disrupted cells, preferably from the cytosol fraction of the microorganism.

The enzyme applied to the process provided by the present invention is useful as a catalyst for the production of vitamin C from L-sorbosone. The reaction may be at pH 60° C. for about 0.5 to 48 hours in the presence of an electron acceptor, for example DCIP, PMS and the like in a solvent such as phosphate buffer, Tris-buffer and the like. A pH of about 7.0 to 8.2 and a temperature in the range of from about 20° C. to 50° C. for about 0.5 to 24 hours are a condition under which L-sorbosone is efficiently converted to vitamin C.

Thus, in the process of the present invention, the reaction is carried out at a pH of about 6.4 to about 9.0 and at a temperature of about 20° C. to about 60° C. for about 0.5 to about 48 h. A preferred reaction is carried out at a pH of about 7.0 to about 8.2 and at a temperature of about 20° C. to about 50° C. for about 0.5 to about 24 h.

The concentration of L-sorbosone in a reaction mixture can vary depending on other reaction conditions but, in general, is about 0.5 to about 50 g/L, preferably from about 1 to about 30 g/L.

According to the present invention the catalytic reaction is carried out in water or Aqueo us solvents such as methanol, ethanol, acetone or mixtures of any one of these solvents and water, however, water is preferred from the view point of economy and easy handling.

In the process of this invention, the enzyme may also be used in an immobilized state with an appropriate carrier. Any means of immobilizing enzymes generally known in the art may be used. For instance, the enzyme may be bound directly to a membrane, granules or the like of a resin having one or more functional groups, or it may be bound to the resin through bridging compounds having one or more functional groups, for example glutaraldehyde.

The produced vitamin C in the reaction mixture may be isolated by conventional methods known in the art, and it may be separated as a salt, e.g., sodium, potassium, calcium, ammonium or the like. This salt may be converted into a free acid by conventional methods known in the art. Specifically, the separation may be performed by any suitable combination or repetition of the following steps: formation of a salt by using differences in properties between the product and the surrounding impurities, such as solubility, absorbability and distribution coefficient between the solvents, and absorption, for example, on ion exchange resin and the like. Any of these procedures alone or in combination constitutes a convenient means for isolating the product. The product thus obtained may further be purified in a conventional manner, e.g., by re-crystallization or chromatography.

The following Examples further illustrate the present invention.

EXAMPLE 1

Preparation of L-sorbosone Dehydrogenase

All the operations were performed at 8° C., and the buffer was 0.05 M potassium phosphate (pH 7.0) unless otherwise stated.

(1) Cultivation of *G. oxydans* DSM 4025 (FERM BP-3812):

*G. oxydans* DSM 4025 (FERM BP-3812) was grown on an agar plate containing 5.0% D-mannitol, 0.25% $MgSO_4.7H_2O$, 1.75% corn steep liquor, 5.0% baker's yeast, 0.5% urea, 0.5% $CaCO_3$ and 2.0% agar at 27° C. for 4 days. One loopful of the cells was inoculated into 50 ml of a seed culture medium containing 2% L-sorbose, 0.2% yeast extract, 0.05% glycerol, 0.25% $MgSO_4.7H_2O$, 1.75% corn steep liquor, 0.5% urea and 1.5% $CaCO_3$ in a 500 ml Erlenmeyer flask, and cultivated at 30° C. with 180 rpm for one day on a rotary shaker.

The cultured broth (10 ml) was transferred into 500 ml Erlenmeyer flasks containing 100 ml of the same seed culture medium and cultivated in the same manner as described above. The seed culture thus prepared was used for inoculating 15 liters of medium, which contained 8.0% L-sorbose, 0.05% glycerol, 0.25% $MgSO_4.7H_2O$, 3.0% corn steep liquor, 0.4% yeast extract and 0.15% antifoam, in 30 L jar fermentor. The fermentation parameters were 800 rpm for the agitation speed and 0.5 vvm (volume of air/volume of medium/minute) for aeration at a temperature of 30° C. The pH was maintained at 7.0 with sodium hydroxide during the fermentation. After 48 h of cultivation, 30 liters of the cultivated broth containing the cells of *G. oxydans* DSM 4025 (FERM BP-3812) by using the two sets of fermentors were harvested by continuous centrifugation. The pellets containing the cells were recovered and suspended in an appropriate volume of saline.

After the suspension was centrifuged at 2,500 rpm (1,000×g), the supernatant containing the cells was recovered to remove the insoluble materials derived from corn steep liquor and yeast extract which were ingredients in the medium. The supernatant was then centrifuged at 8,000 rpm (10,000×g) to obtain the cell pellet. As a result, 123 g of *G. oxydans* DSM 4025 (FERM BP-3812) cells (wet weight) was obtained from 30 liters of broth.

(2) Preparation of Cytosol Fraction:

The cell pellet (64.2 g) was suspended with 280 ml of the buffer and passed through a French pressure cell press. After centrifugation to remove intact cells, the supernatant was designated as the cell-free extract, and the cell-free extract was centrifuged at 100,000×g for 60 min. The resultant supernatant (227 ml) was designated as the soluble fraction of *G. oxydans* DSM 4025 (FERM BP-3812). After this fraction was dialyzed against the buffer, 150 ml of the dialyzed fraction having a specific activity of 0.107 unit/mg protein were used for the next purification step.

(3) Diethylaminoethyl (DEAE)-cellulose Column Chromatography:

The dialysate (150 ml) was put on a column of DEAE-cellulose (Whatman DE-52, 3×50 cm) equilibrated and washed with the buffer to elute minor proteins. Then proteins bound to the resin were eluted stepwise with 0.28, 0.32, 0.36 M NaCl in the buffer. Major enzyme activity was eluted at 0.36 M NaCl. The active fractions (143 ml) were collected.

(4) Carboxymethyl-cellulose Column Chromatography:

A portion (127 ml) of the active fraction from the previous step was filtrated by an ultrafiltrator (Centriprep-10, Amicon) to concentrate. After the concentrated sample (28 ml) was dialyzed against the buffer, 28 ml of the dialyzed fraction (31 ml) was put on a column of carboxymethyl-cellulose (Whatman CM-52, 3×23 cm) equilibrated with the buffer. The proteins that passed through the column without binding to the resin were collected.

(5) Q-sepharose Column Chromatography (#1):

The pooled active fraction (43 ml) was concentrated by an ultrafiltrator (Centriprep-10). A portion (9.5 ml) of the concentrated fraction (10 ml) from the previous step was put on a column of Q-sepharose (Pharmacia, 1.5 by 50 cm) equilibrated with the buffer. After the column was washed with the buffer containing 0.3 M NaCl, a linear gradient of NaCl from 0.3 to 0.6 M was added to the buffer. The active fractions were eluted at NaCl concentrations ranging from 0.55 to 0.57 M.

(6) Q-sepharose Column Chromatography (#2):

The pooled active fraction (22 ml) from the previous step was concentrated by an ultrafiltrator (Centriprep-10). The concentrate (3.0 ml) was dialyzed against the buffer. The dialyzed sample (3.5 ml) was put on a column of Q-sepharose (Pharmacia, 1.5 by 50 cm) equilibrated with the buffer. After the column was washed with the buffer containing 0.35 M NaCl, a linear gradient of NaCl from 0.35 to 0.7 M was added to the buffer. The active fractions were eluted at NaCl concentrations ranging from 0.51 to 0.53 M.

(7) Gel Filtration (Sephacryl S-300 High Resolution) Column Chromatography:

The pooled active fraction (20 ml) from the previous step was concentrated by an ultrafiltrator (Centriprep-10). A 1.5 ml portion of the concentrated and desalted (below 0.1 M NaCl) sample (2.0 ml) was put on a column of Sephacryl S-300 High Resolution (Pharmacia, 1.5 by 120 cm) equilibrated with the buffer containing 0.1 M NaCl. The active fractions (12 ml) were collected and dialyzed against the buffer.

(8) Hydrophobic Column (RESOURCE ISO) Chromatography:

The dialyzed active fraction from the previous step was concentrated by an ultrafiltrator (Centriprep-10). A portion (1.5 ml) of the concentrated sample (1.75 ml) was added to the equal volume (1.5 ml) of the buffer containing 3 M ammonium sulfate (final concentration: 1.5 M). After centrifugation (15,000×g) of the sample, the supernatant was loaded on a column RESOURCE ISO (Pharmacia, 1.0 ml) equilibrated with the buffer containing 1.5 M ammonium sulfate. After the column was washed with the buffer containing 1.5 M ammonium sulfate, the proteins were eluted with the buffer containing a linear gradient of ammonium sulfate from 1.5 to 0.75 M. The active fractions corresponding to the L-sorbosone dehydrogenase were eluted at ammonium sulfate concentrations ranging from 1.12 to 1.10 M. The active fractions were dialyzed against the buffer using dialysis cups (Dialysis-cup MWCO 8000, Daiichi pure chemicals). Afterwards, the fractions were collected and stored at −20° C. A summary of the purification steps of the enzyme is given in Table 1.

TABLE 1

Purification of the aldehyde dehydrogenase from *G. oxydans* DSM 4025 (FERM BP-3812)

| Step | Total activity (units) | Total protein (mg) | Specific activity (units/mg protein) |
|---|---|---|---|
| Soluble fraction | 343.0 | 3205.2 | 0.107 |
| DEAE-Cellulose DE52 | 26.10 | 120.67 | 0.216 |
| CM-Cellulose CM52 | 28.86 | 105.70 | 0.273 |
| Q-Sepharose (#1) | 38.94 | 12.56 | 3.100 |
| Q-Sepharose (#2) | 10.77 | 3.47 | 3.102 |
| Sephacryl S-300HR | 9.09 | 0.71 | 12.81 |
| RESOURCE ISO | 3.71 | 0.12 | 31.71 |

EXAMPLE 2

Influence of pH on the Reaction Products from L-sorbosone

The reaction mixture consisting of the purified enzyme (0.42 μg), L-sorbosone (50 mM), PMS (1 mM), CaCl$_2$ (1 mM) and PQQ (1 μM) in 100 μl of 100 mM various buffers was incubated for 1 h at 30° C. The reaction products were analyzed by thin layer chromatography (Silica gel 60F$_{254}$, MERCK) and HPLC. The vitamin C production was detected in the pH range from 6.4 to around 8.0. On the other hand, 2-KGA production was detected in the pH range from 5.4 to around 9.0 as shown in Table 2.

TABLE 2

Influence of pH on the reaction products from L-sorbosone

| Buffers used | pH set (—) | Vitamin C produced (mg/L) | 2-KGA produced (mg/L) |
|---|---|---|---|
| Citrate-NaOH | 4.4 | 0.0 | 0.0 |
| | 5.4 | 0.0 | 21.5 |
| | 6.4 | 6.5 | 5.1 |
| Potassium phosphate | 6.6 | 11.9 | 5.0 |
| | 7.1 | 29.0 | not done |
| | 7.4 | 48.8 | 9.6 |
| | 7.8 | 38.8 | 17.6 |
| | 8.2 | 21.0 | 24.8 |
| Tris-HCl | 7.9 | 19.5 | 92.3 |
| | 8.4 | 0.0 | 106.3 |
| | 8.9 | 0.0 | 147.5 |

EXAMPLE 3

Effect of Temperature on the Activity

The reaction mixture containing 0.42 μg of the purified L-sorbosone dehydrogenase, 50 mM L-sorbosone, 1 μM PQQ, 1 mM CaCl$_2$, 1 mM PMS in 25 mM potassium phosphate buffer (pH 7.0) was incubated for 60 min at various temperatures. converted to vitamin C and 2-KGA as shown in Table 3.

TABLE 3

Effect of temperature on the conversion activity of L-sorbosone to vitamin C and 2-KGA

| Temperature (° C.) | Vitamin C produced (mg/L) | 2-KGA produced (mg/L) |
|---|---|---|
| 20 | 148.6 | 36.1 |
| 25 | 111.1 | 32.6 |
| 30 | 115.9 | 34.4 |
| 35 | 107.8 | 30.3 |
| 40 | 141.4 | 35.4 |
| 50 | 111.4 | 41.5 |
| 60 | 6.4 | 20.6 |

The invention claimed is:

1. A process for producing vitamin C from L-sorbosone which comprises contacting L-sorbosone with a purified L-sorbosone dehydrogenase having the following physicochemical properties:
   a) Molecular weight: 150,000±6,000 Da or 230,000±9,000 Da (consisting of 2 or 3 homologous subunits, each subunit having a molecular weight of 75,000±3,000 Da)
   b) Substrate specificity: active on aldehyde compounds
   c) Cofactors: pyrroloquinoline quinone and heme c
   d) Optimum pH: 6.4 to 8.2 for the production of vitamin C from L-sorbosone
   e) Inhibitors: $Co^{2+}$, $Cu^{2+}$, $Fe^2$, $Ni^2$, $Zn^2$, monoiodoacetate and ethylenediamine tetraacetic acid, wherein the conversion of L-sorbosone to vitamin C is catalyzed by the purified L-sorbosone dehydrogenase in the presence of an electron acceptor, and isolating the resulting vitamin C from the reaction mixture.

2. The process for producing vitamin C from L-sorbosone according to claim 1, wherein the L-sorbosone dehydrogenase is derived from the strain *Gluconobacter oxydans* DSM No. 4025 (FERM BP-3812), a microorganism belonging to the genus *Gluconobacter* having identifying characteristics to *G. oxydans* DSM 4025 (FERM BP-3812) or its mutants.

3. The process according to claim 1, wherein the contacting of L-sorbosone with a purified L-sorbosone dehydrogenase is carried out at pH values of about 6.4 to about 9.0 and at a temperature range from about 20° C. to 60° C. for about 0.5 to 48 hours.

4. The process according to claim 1, wherein the contacting of L-sorbosone with a purified L-sorbosone dehydrogenase is carried out at pH values of about 7.0 to 8.2 and at a temperature range from about 20° C. to 50° C. for about 0.5 to 24 hours.

5. The process according to claim 1, wherein the contacting of L-sorbosone with a purified L-sorbosone dehydrogenase is carried out at pH values of about 7.0 and at a temperature range from about 20° C. to 50° C.

6. The process according to claim 1, wherein the contacting of L-sorbosone with a purified L-sorbosone dehydrogenase is carried out for about 1 hour.

7. The process according to claim 1, wherein the contacting of L-sorbosone with a purified L-sorbosone dehydrogenase is carried out at pH values of about 6.6 to 7.8 and at a temperature of about 30° C. for about 1 hour.

8. The process according to claim 7, wherein the contacting of L-sorbosone with a purified L-sorbosone dehydrogenase is further carried out in the presence of 100 mM potassium phosphate.

* * * * *